United States Patent
Downie

(10) Patent No.: US 10,499,886 B1
(45) Date of Patent: Dec. 10, 2019

(54) PORTABLE SCALE SYSTEM TO WEIGH WASTE

(71) Applicant: Terence James Downie, San Ramon, CA (US)

(72) Inventor: Terence James Downie, San Ramon, CA (US)

( * ) Notice: Subject to any disclaimer, the term of this patent is extended or adjusted under 35 U.S.C. 154(b) by 229 days.

(21) Appl. No.: 15/835,787

(22) Filed: Dec. 8, 2017

(51) Int. Cl.
| | | |
|---|---|---|
| *G01G 19/52* | (2006.01) | |
| *A61B 10/00* | (2006.01) | |
| *E03D 9/00* | (2006.01) | |
| *G01N 33/483* | (2006.01) | |

(52) U.S. Cl.
CPC ......... *A61B 10/0038* (2013.01); *G01G 19/52* (2013.01); *E03D 9/00* (2013.01); *G01N 33/483* (2013.01)

(58) Field of Classification Search
CPC ........ G01G 19/44; G01G 19/52; G01G 19/60; A61B 10/0038; E03D 9/00; G01N 33/483
See application file for complete search history.

(56) References Cited

U.S. PATENT DOCUMENTS

| | | | | | |
|---|---|---|---|---|---|
| 2,057,024 A | * | 10/1936 | Gunnison | ............... | G01G 19/44 177/144 |
| 2,617,996 A | * | 11/1952 | Hoffman | ................... | E03D 9/00 4/256.1 |
| 3,540,433 A | * | 11/1970 | Brockman | ......... | A61B 10/0038 600/562 |
| 3,754,287 A | * | 8/1973 | Taylor | .................... | A47K 17/00 4/661 |
| 3,860,971 A | * | 1/1975 | Dirks | ..................... | A47K 17/00 68/235 D |
| 4,697,656 A | * | 10/1987 | de Canecaude | ....... | G01G 19/44 177/144 |
| 4,819,277 A | * | 4/1989 | Sikirov | ................... | A47K 13/24 4/239 |
| 5,463,782 A | * | 11/1995 | Carlson | ............. | A61B 10/0038 4/661 |
| 5,854,447 A | * | 12/1998 | Greenwood | ........... | A01K 77/00 177/25.14 |
| 6,094,996 A | * | 8/2000 | Campbell | .............. | A01K 77/00 73/862.474 |
| 6,523,187 B1 | * | 2/2003 | Brink | ..................... | A47K 11/06 383/37 |
| 6,640,355 B1 | * | 11/2003 | Samide | .............. | A61B 10/0038 4/144.2 |
| 7,437,781 B2 | * | 10/2008 | Rigas | ..................... | A47K 13/24 177/144 |
| 7,856,676 B2 | * | 12/2010 | Akagi | ...................... | A61B 1/04 210/238 |
| 8,093,515 B2 | * | 1/2012 | Pigott | ................... | G01G 19/60 177/148 |
| 9,456,585 B1 | * | 10/2016 | Kao | ....................... | A01K 23/005 |
| 9,476,758 B2 | * | 10/2016 | Jones | ................... | G06T 1/0007 |

(Continued)

*Primary Examiner* — Randy W Gibson
(74) *Attorney, Agent, or Firm* — Plager Schack LLP; Mark H. Plager; Alexis J. Saenz

(57) ABSTRACT

A scale system includes a frame for placement over a toilet and a net to catch waste, for example from bowel movements. A scale is connected to the frame to register a change in tension experienced by the frame as waste is received by the net. The resulting weight measurement may be shown on a digital display. Once the user is done, a release lever on the frame may be triggered to release the net and waste into the toilet.

4 Claims, 3 Drawing Sheets

(56) References Cited

U.S. PATENT DOCUMENTS

| | | | |
|---|---|---|---|
| 9,595,185 B1* | 3/2017 | Hall | E03D 5/10 |
| 9,927,302 B1* | 3/2018 | Hall | G01J 5/041 |
| 10,190,903 B2* | 1/2019 | Lebedev | G01G 19/00 |
| 2007/0074992 A1* | 4/2007 | Fukuda | A61B 10/0038 |
| | | | 206/528 |
| 2019/0059860 A1* | 2/2019 | Shahaf | A47K 11/105 |

* cited by examiner

PORTABLE SCALE SYSTEM TO WEIGH WASTE

CROSS-REFERENCE TO RELATED APPLICATIONS

None.

BACKGROUND

The embodiments herein relate generally to measurement systems and more particularly, to a portable scale to weight waste.

While there exist a number of various types of scales, the current scale configurations are not suitable for measuring bodily waste. Typically, a scale has a solid platform or container. A user engaging in a bowel movement may need to catch the waste manually using a plastic bag or other container because flat scales or open-ended containers then placed on a scale are awkward to use for receiving waste. Flat scales or open-ended containers become dirty and generally undesirable to wash and re-use. Embodiments, solve these problems.

SUMMARY

In one aspect of the subject disclosure, a scale system for measuring waste comprises a frame including a pair of arms and an opening between the pair of arms. A net may be disposed between the pair of arms. A fastener system may be configured to secure the net to the pair of arms so that the net spans across the opening between the pair of arms. A scale may be attached to the frame and configured to measure weight received in the net. A display may be included which shows a measured weight result of waste received in the net.

BRIEF DESCRIPTION OF THE FIGURES

The detailed description of some embodiments of the invention is made below with reference to the accompanying figures, wherein like numerals represent corresponding parts of the figures.

DETAILED DESCRIPTION OF CERTAIN EMBODIMENTS

Figure 1:
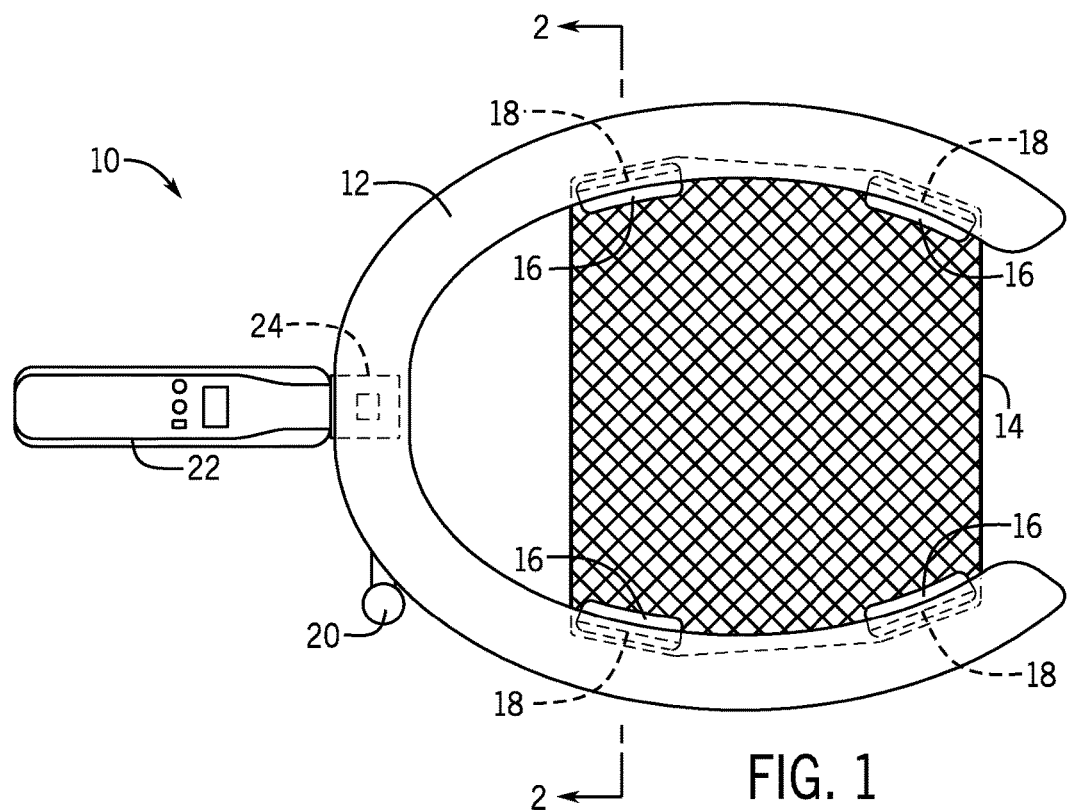
FIG. 1 is a top plan view of a scale according to an embodiment of the subject technology.
Figure 2:
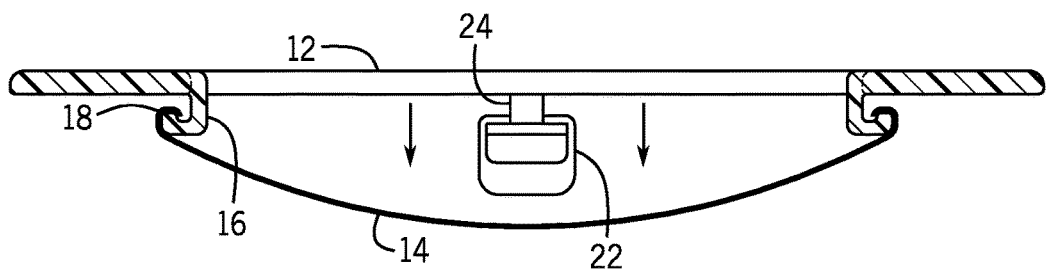
FIG. 2 is a cross-sectional view taken along the line 2-2 of FIG. 1.

In general, embodiments of the disclosed invention provide a portable scale which may be hand-held and used to weigh animal waste, and more particularly for example, human waste. Referring now to FIGS. 1-2, an exemplary embodiment of a scale system 10 is shown. The scale system 10 may in one configuration include a frame 12 adapted to fit over a toilet (not shown). The frame 12 may for example, be substantially U-shaped with a pair of arms and an open end similar to the shape of a toilet seat. A net 14 may span across an opening between the arms of frame 12. The net 14 may include latches 18 on its periphery which may secure the net 14 into place on the frame 12 by being attached to hooks 16 on undersides of opposing frame 12 arms (FIG. 2). A manual release lever 20 may be included which when operated causes the hooks 16 to press inward toward opposing hooks 16 so that the tension holding the net 14 in place is relaxed and the latches 18 disengage from the hooks 16.

Figure 3:
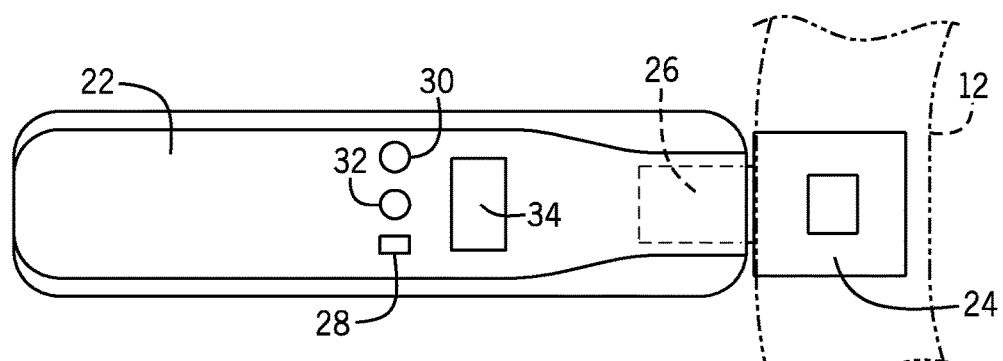
FIG. 3 is a partial, sectional top view of a control device on the handle of the scale of FIG. 1.
Figure 4:
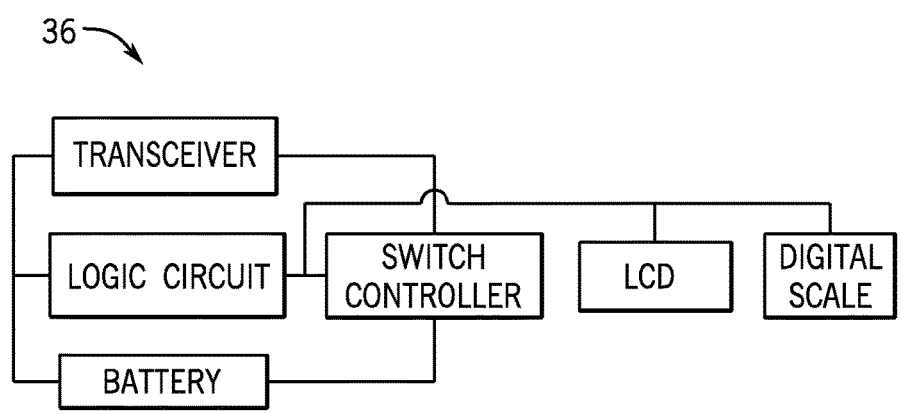
FIG. 4 is a block diagram showing electrical connections among elements of a scale according to an embodiment of the subject technology.
Figure 5:
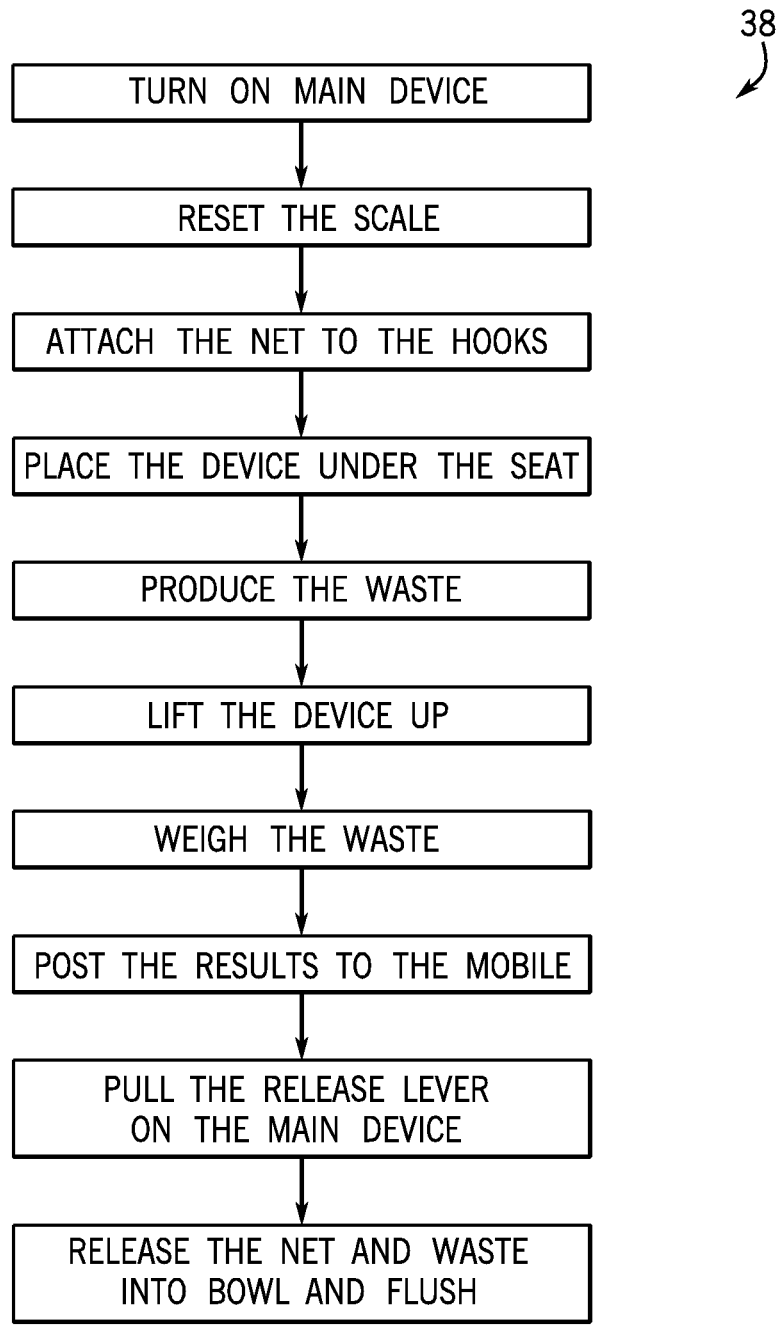
FIG. 5 is a flowchart of a method of operating a scale according to another embodiment.

Referring now to FIGS. 3 and 4, in one aspect, the scale system 10 may be used to measure, record and track weight of expelled waste. FIG. 3 shows an enlarged view of electrical components attached the frame 12. FIG. 4 shows a connection scheme 36 for electrical components according to an exemplary embodiment. In an exemplary embodiment, the scale system 10 may include a handle projecting rearwardly from the arms. The handle may include an electrical controller 22. The controller 22 may include a scale 26 (passive or electronic) which may be attached to the arms of frame 12. A logic circuit may process data received by the scale 26 and provide processed data for display and transmission. For example, in operation (and referring concurrently to the method 38 of FIG. 5), a user may initialize the scale system 10 by pressing an on/off switch 28. The user may reset a previous reading by pressing a reset button 32 which causes the logic circuit to zero out an LCD display 34. The user may produce a bowel movement over the scale system 10 set over a toilet (not shown). The waste expelled may be caught by the net 14 and the resulting weight of the waste may produce an increased tension in the arms which is registered by the connected scale 26. The signal from the scale 26 may be provided to the logic circuit which may be programmed to display the result on the LCD display 34. In some embodiments, the scale system 10 may include a transceiver that in response to the user pressing a post results button 30, wirelessly transmits the weight result via a radio signal to a mobile software application host computing device or social media account so that others may see the results. Once done, the user may press the release lever 20 which releases the net 14 and waste into the toilet for disposal. The user may open up the aforementioned mobile software application to see results. The application may in some embodiments store a history of past weights recorded, track weights, provide comparisons to other users, and provide analytics for the user's "performance".

Aspects of the disclosed invention are described below with reference to block diagrams of methods, apparatus (systems) and computer program products according to embodiments of the invention. It will be understood that each block of the block diagrams, and combinations of blocks in the flowchart illustrations and/or block diagrams, can be implemented by computer program instructions. These computer program instructions may be provided to the processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

As will be appreciated by one skilled in the art, aspects of the disclosed invention may be embodied as a system, method or process, or computer program product. Accordingly, aspects of the disclosed invention may take the form of an entirely hardware embodiment, an entirely software embodiment (including firmware, resident software, microcode, etc.) or an embodiment combining software and hardware aspects that may all generally be referred to herein as a "circuit," "module," or "system." Furthermore, aspects of the disclosed invention may take the form of a computer program product embodied in one or more computer readable media having computer readable program code embodied thereon.

Any combination of one or more computer readable media may be utilized. In the context of this disclosure, a computer readable storage medium may be any tangible or non-transitory medium that can contain, or store a program for use by or in connection with an instruction execution system, apparatus, or device. A computer readable storage medium may be, for example, but not limited to, an electronic, magnetic, optical, electromagnetic, infrared, or semiconductor system, apparatus, or device, or any suitable combination of the foregoing.

Persons of ordinary skill in the art may appreciate that numerous design configurations may be possible to enjoy the functional benefits of the inventive systems. Thus, given the wide variety of configurations and arrangements of embodiments of the present invention the scope of the invention is reflected by the breadth of the claims below rather than narrowed by the embodiments described above.

What is claimed is:

1. A scale system for measuring waste, comprising:
   a frame including a pair of arms and an opening between the pair of arms;
   a net disposed between the pair of arms;
   a fastener system configured to secure the net to the pair of arms, wherein the net spans across the opening between the pair of arms;
   a scale attached to the frame and configured to measure weight received in the net; and
   a display showing a measured weight result of waste received in the net.

2. The scale system of claim 1, further comprising:
   a logic circuit connected to the scale; and
   a transceiver configured to transmit the measured weight result when processed by the logic circuit to an application software host computing device for display to third parties.

3. The scale system of claim 1, further comprising a release lever connected to the arms and configured to release the net from the pair of arms.

4. The scale system of claim 1, further comprising a handle attached to the frame, the handle including a logic circuit connected to the scale, wherein the logic circuit is configured to process weight data registered by the scale.

* * * * *